(12) United States Patent
Olson et al.

(10) Patent No.: US 11,553,932 B2
(45) Date of Patent: Jan. 17, 2023

(54) CAPTURED SLOTTED REAMER

(71) Applicant: Howmedica Osteonics Corp., Mahwah, NJ (US)

(72) Inventors: Nicholas Olson, Belleville, NJ (US); Andrew J. Nelson, New City, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 459 days.

(21) Appl. No.: 16/720,218

(22) Filed: Dec. 19, 2019

(65) Prior Publication Data

US 2020/0121329 A1 Apr. 23, 2020

Related U.S. Application Data

(63) Continuation of application No. 15/476,251, filed on Mar. 31, 2017, now Pat. No. 10,548,617.

(51) Int. Cl.
*A61B 17/00* (2006.01)
*A61B 17/16* (2006.01)
*A61B 17/17* (2006.01)

(52) U.S. Cl.
CPC ...... *A61B 17/1642* (2013.01); *A61B 17/1684* (2013.01); *A61B 17/17* (2013.01)

(58) Field of Classification Search
CPC combination set(s) only.
See application file for complete search history.

(56) References Cited

U.S. PATENT DOCUMENTS

| | | |
|---|---|---|
| 3,559,514 A | 2/1971 | Brownfield |
| 5,203,653 A | 4/1993 | Kudla |
| 7,294,133 B2 | 11/2007 | Zink et al. |
| 8,414,586 B2 | 4/2013 | Cawthan et al. |
| 8,486,076 B2 | 7/2013 | Chavarria et al. |
| 8,523,867 B2 | 9/2013 | Rauscher et al. |

(Continued)

FOREIGN PATENT DOCUMENTS

| | | |
|---|---|---|
| DE | 3404123 A1 | 6/1985 |
| DE | 69606847 T2 | 8/2000 |

(Continued)

OTHER PUBLICATIONS

Global APG+ Instrumentation, Joint Reconstruction, Surgical Technique, DePuy Synthes, Mar. 2014.

*Primary Examiner* — Sameh R Boles
(74) *Attorney, Agent, or Firm* — Lerner, David, Littenberg, Krumholz & Mentlik, LLP

(57) ABSTRACT

Described herein are cannulated reamer designs and methods. In one embodiment, a reamer comprises a cannulated central body portion, a plurality of cutting legs and outer frame. The cannulated central body portion has an inner wall surface and an opposing outer wall surface defining a thickness and a bone contacting surface and an opposing distal end surface defining a length, the inner wall surface defining a bore about a central longitudinal axis of the cannulated central body portion. The plurality of cutting legs extends outwardly from the cannulated central body portion. The other defines a periphery of the reamer, the outer frame coupled to a lateral end of each of the plurality of cutting legs. The cannulated central body portion has a recess extending entirely through the thickness and only partially though the length.

11 Claims, 6 Drawing Sheets

(56) References Cited

U.S. PATENT DOCUMENTS

| | | | |
|---|---|---|---|
| 9,080,611 | B2 | 7/2015 | Sander |
| 2003/0163135 | A1 | 8/2003 | Hathaway |
| 2004/0236339 | A1 | 11/2004 | Pepper |
| 2006/0015110 | A1 | 1/2006 | Pepper |
| 2006/0058809 | A1 | 3/2006 | Zink et al. |
| 2007/0038303 | A1 | 2/2007 | Myerson et al. |
| 2008/0300600 | A1 | 12/2008 | Guelat et al. |
| 2008/0306482 | A1 | 12/2008 | Muller |
| 2009/0270863 | A1 | 10/2009 | Maisonneuve |
| 2010/0145342 | A1 | 6/2010 | Grace et al. |
| 2010/0280517 | A1 | 11/2010 | Cawthan et al. |
| 2012/0123419 | A1* | 5/2012 | Purdy ................ A61B 17/1615 606/83 |

FOREIGN PATENT DOCUMENTS

| | | |
|---|---|---|
| DE | 69524703 T2 | 8/2002 |
| DE | 102005058107 A1 | 7/2007 |
| DE | 102012208816 B4 | 9/2014 |
| EP | 2666418 A3 | 1/2014 |
| EP | 2730239 A1 | 5/2014 |
| EP | 2231033 B1 | 9/2014 |
| EP | 2459081 B1 | 8/2015 |
| FR | 2967046 A1 | 5/2012 |
| GB | 2406278 B | 8/2007 |
| WO | 2007097749 A1 | 8/2007 |
| WO | 2009083707 A1 | 7/2009 |
| WO | 2011012318 A1 | 2/2011 |
| WO | 2014134584 A1 | 9/2014 |

\* cited by examiner

CAPTURED SLOTTED REAMER

CROSS REFERENCE TO RELATED APPLICATIONS

The present application is a continuation of U.S. patent application Ser. No. 15/476,251, filed Mar. 31, 2017, the disclosure of which is incorporated herein by reference.

FIELD OF THE INVENTION

The present invention relates in general to reamers for shoulder arthroplasty and in particular to reamers for use in minimally invasive shoulder arthroplasty procedures.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint tear becomes damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region. Arthroplasty procedures may take place in any of a number of different regions of the body, such as the knees, hips, shoulders, or elbows, for example.

One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation and/or patient-specific guides may be used for locating a position and orientation to resect the humeral head for proper humeral stem placement.

Accuracy in implant alignment is an important factor to the success of a surgical procedure. A one to two millimeter translational misalignment, or a one to two degree rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. Prior to reaming the scapula, for example, the trajectory that the reaming will take place is determined either preoperatively or intraoperatively. A reamer is generally slid over a guide wire placed in the scapula at a desired trajectory. The reamer is then preferably used to remove bone at that trajectory until a desired depth is reached. Dislocation of the shoulder joint between the humerus and scapula generally occurs prior to reaming. It is often desirable to limit the amount of dislocation of the shoulder joint in order to not damage and/or preserve the surrounding soft tissues.

BRIEF SUMMARY OF THE INVENTION

A first aspect of the invention is a reamer comprising a cannulated central body portion, a plurality of cutting legs and an outer frame. The cannulated central body portion has an inner wall surface and an opposing outer wall surface defining a thickness and a bone contacting surface and an opposing distal end surface defining a length, the inner wall surface defining a bore about a central longitudinal axis of the cannulated central body portion. The plurality of cutting legs extends outwardly from the cannulated central body portion. The outer frame defines a periphery of the reamer, the outer frame being coupled to a lateral end of each of the plurality of cutting legs. The cannulated central body portion has a recess extending entirely through the thickness and only partially though the length from a location along the length above the bone contacting surface and through the opposing distal end surface.

In one embodiment of the first aspect, the bore and the recess form a transverse inner opening for receipt of a guide pin at an angle to the central longitudinal axis. The recess is u-shaped and defined by a curved base surface intermediate first and second planar surface sections.

In another embodiment of the first aspect, the recess is defined by a base surface intermediate first and second planar surface sections, the first and second planar sections separated by a width of the recess. The recess has a length defined by a linear distance between the opposing distal end surface and the base surface of the recess.

In yet another embodiment of the first aspect, the plurality of cutting legs are each coupled at a medial end thereof to the bone contacting surface of the cannulated central body portion.

In still yet another embodiment of the first aspect, the opposing outer wall surface of the cannulated central body is circular and the plurality of cutting legs extend radially from the opposing outer wall surface.

In still yet another embodiment of the first aspect, a plurality of reamer apertures are defined by the opposing outer wall surface of the cannulated body portion, adjacent cutting legs and the outer frame. The recess and one of the plurality of reamer apertures form a transverse outer opening for receipt of a guide pin at an angle to the central longitudinal axis.

A second aspect of the invention is a reamer system comprising a reamer and a guide pin. The reamer has a cannulated central body portion having an inner wall surface and an opposing outer wall surface defining a thickness and a bone contacting surface and an opposing distal end surface defining a length, a recess extending entirely through the thickness and only partially though the length from a location along the length above the bone contacting surface and through the opposing distal end surface, the inner wall surface defining a bore about a central longitudinal axis of the cannulated central body portion. The guide pin has a diameter and a length, the diameter of the guide pin being less than a width of the recess, wherein the bore and the recess form a transverse opening for receipt of the guide pin at an angle to the central longitudinal axis.

In one embodiment of this second aspect, the recess is u-shaped and defined by a curved base surface intermediate first and second planar surface section.

In another embodiment of this second aspect, the recess is defined by a base surface intermediate first and second planar surface sections, the first and second planar sections separated by a width of the recess.

In yet another embodiment of this second aspect, the recess has a length defined by a linear distance between the opposing distal end surface and the base surface of the recess.

In still yet another embodiment of this second aspect, the plurality of cutting legs are each coupled at a medial end thereof to the bone contacting surface of the cannulated central body portion.

In still yet another embodiment of this second aspect, the opposing outer wall surface of the cannulated central body is circular and the plurality of cutting legs extend radially from the opposing outer wall surface.

A third aspect of the invention is a minimally invasive reaming method comprising sliding a guide pin at an angle to a central longitudinal axis of a reamer through a transverse opening in a cannulated central body portion of the reamer, the cannulated central body portion having a recess through an inner wall surface, an opposing outer wall surface, and a distal end surface, the inner wall surface defining a bore having a central longitudinal axis, the bore and the recess together forming the transverse opening; positioning a bone contacting surface of the reamer against a desired bone to be reamed; rotating the guide pin until a central axis of the guide pin is substantially co-linear with the central longitudinal axis of the bore of the reamer, wherein the cannulated central body portion has a recess extending entirely through the thickness and only partially though the length from a location along the length above the bone contacting surface and through the opposing distal end surface.

In one embodiment of this third aspect, the reaming method further comprises sliding a cannulated shaft over the guide pin until the cannulated shaft is coupled to the reamer, the cannulated shaft closing the recess.

BRIEF DESCRIPTION OF THE DRAWINGS

Other objects and advantages of the present invention will be apparent from the following detailed description of the present preferred embodiments, which description should be considered in conjunction with the accompanying drawings in which like reference indicate similar elements and in which.

DETAILED DESCRIPTION

Figure 1A:
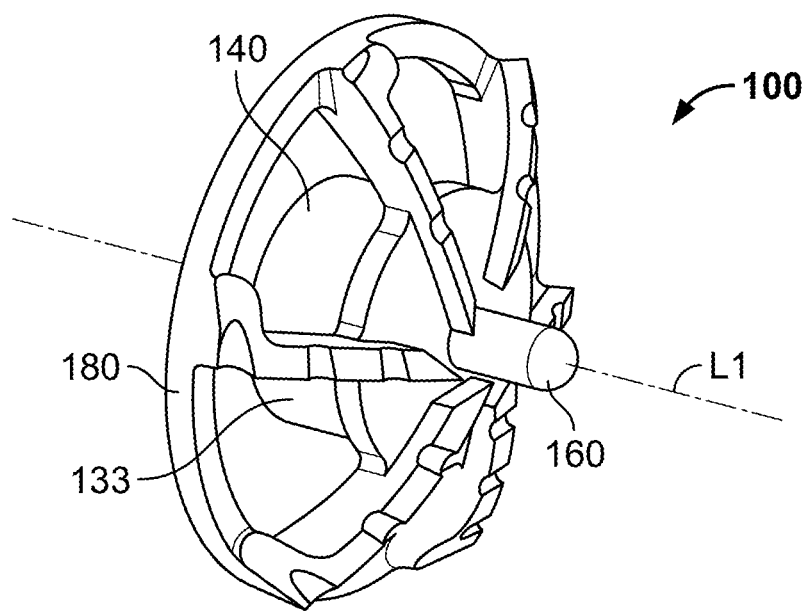
FIG. 1A is a perspective view of one embodiment of a reamer assembly of the disclosure.
Figure 1B:
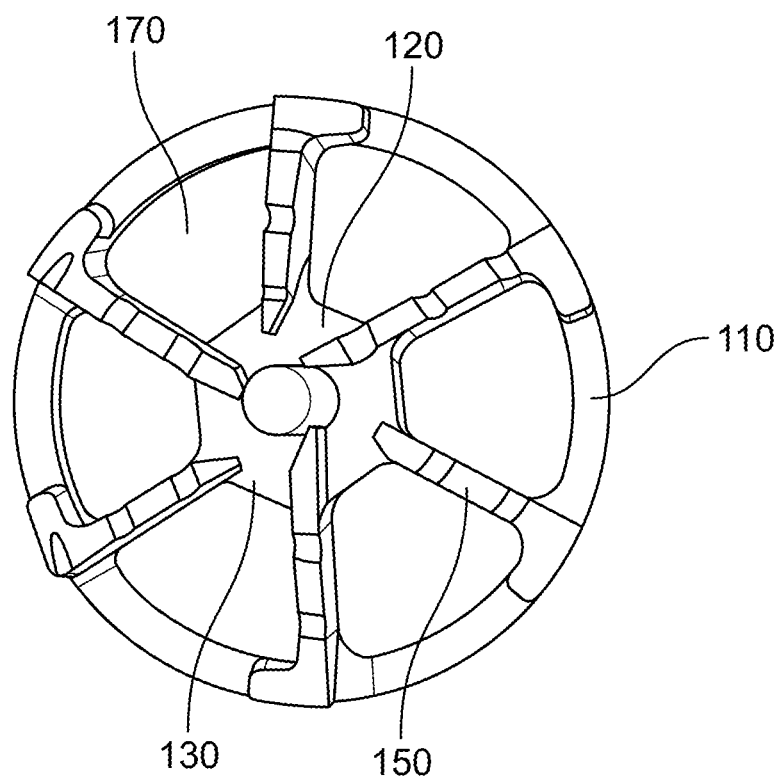
FIG. 1B is a bottom perspective view of the reamer assembly of FIG. 1A.

FIGS. 1A-1D show one embodiment of a reamer assembly 100 including a reamer body 110, a magnet 132 and a reamer housing 133. When assembled together, a portion of reamer body 110 and reamer housing 133 form a central body portion 120 having a bone contacting surface 130 and an opposing distal end surface 140. Reamer body 110 includes a plurality of cutting legs 150 and an outer frame 180. A central positioning portion 160 protrudes outwardly from the bone contacting surface 130 and defines a longitudinal axis L1 of reamer assembly 100 which is coaxial with a desired reaming trajectory of a shoulder arthroplasty procedure. A space 170 is defined by central body portion 120, adjacent cutting legs 150 and outer frame 180.

Figure 1C:
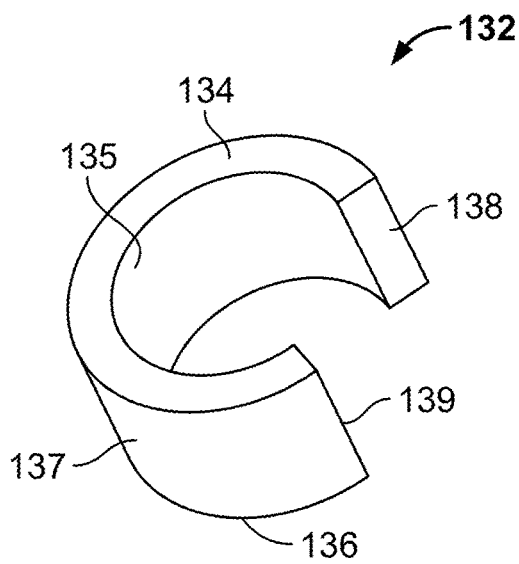
FIG. 1C is a perspective view of one embodiment a reamer magnet of the reamer assembly shown in FIG. 1A.
Figure 1D:
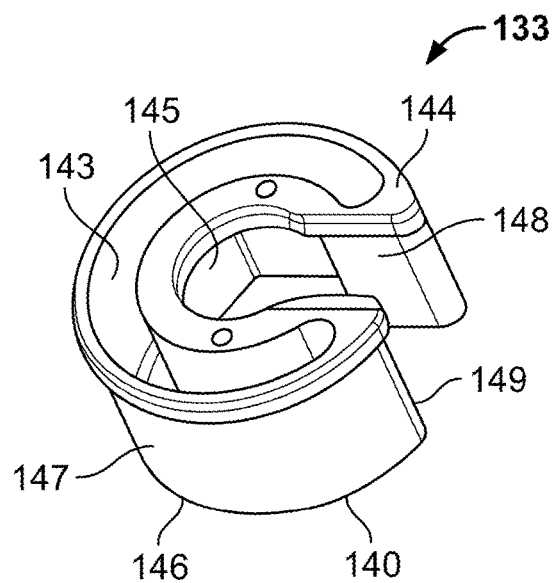
FIG. 1D is a perspective view of one embodiment of a reamer housing of the reamer assembly of FIG. 1A.

As shown in FIG. 1C, magnet 132 includes an upper surface 134, an inner surface 135, a lower surface 136, an outer surface 137 and opposed side surfaces 138, 139 defining a space therebetween. As shown in FIG. 1D, reamer housing 133 includes an upper surface 144, an inner surface 145, a lower surface 146, an outer surface 147 and opposed side surfaces 148, 149 defining a space therebetween. A slot 143 is defined in reaming housing 133 for receipt of magnet 132.

In use, magnet 132 is received in slot 143 of reamer housing 133 and reamer housing 133 is then coupled to an inner surface of reamer body 110. A magnetic connection between reamer housing 133 having magnet 132 therein and metallic reamer body 110 is formed. The bone contacting or cutting surface 120 of reamer body 110 is preferably a hard, magnetic 400 series stainless steel. Magnet 132 is housed in soft, non-magnetic stainless steel housing 133. Magnet 132 itself is shaped in a ring for two purposes. First, the ring shape of magnet 132 is preferable for receipt of a pilot wire or k-wire that can be inserted through reamer assembly 100. A shoulder pilot wire, for example, made from a 316L material does not affect the magnetic field generated by magnet 132. Second, the ring shape of magnet 132 spreads the magnetic field over a larger area and can be used by a flange on a driver to couple reamer assembly 100 to the driver. Reamer assembly 100 including magnet 132 only generates a magnetic field out of the wound along an axis of the driver co-axial with L1. By making reamer assembly 100 from a magnetic and non-magnetic material the field of magnet 132 is generated along the axis of the driver and away from the midline of the patient. A problem with a magnetic instrument in or near shoulder 10, for example, is that it could interfere with any implanted cardiac devices that the patient may have. By directing the magnetic field away from the heart, this risk is mitigated.

The use of magnet 132 in reamer assembly 100 allows reamer assembly 100 to be coupled to a reamer driver non-mechanically. Mechanical connection could be easily damaged and difficult to use, and in most cases, surgeons are instructed to make the mechanical connection outside of the body. Reamer assembly 100 allows it to easily be coupled to a reamer in situ and is repeatable over time.

Figure 2:
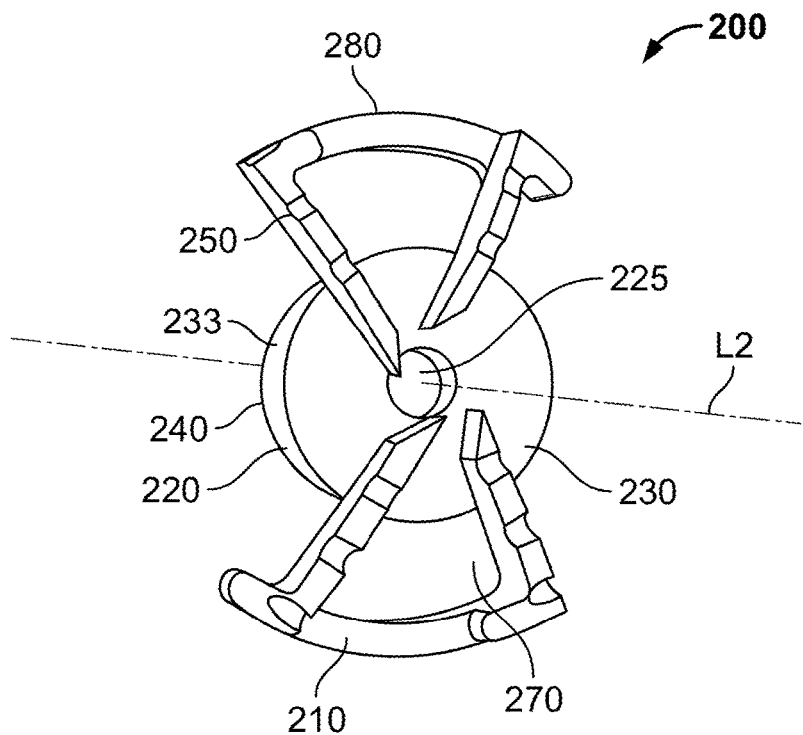
FIG. 2 is a bottom perspective view of another embodiment of a magnetized reamer of the disclosure.

Reamer assembly 200, shown in FIG. 2, is similar to reamer assembly 100, but instead is cannulated and includes an open outer frame 280. Reamer assembly 200 includes a reamer body 210, a magnet (not shown; within reamer housing 233) and a reamer housing 233. When assembled together, a portion of reamer body 210 and reamer housing 233 form a central body portion 220 having a bone contacting surface 230 and an opposing distal end surface 240. Reamer body 210 includes a plurality of cutting legs 250 and an outer frame 280 that forms opposing first and second frame portions. A cannulated aperture 225 is located in a central portion of reamer assembly 200 and defines a longitudinal axis L2 of reamer assembly 200 which is coaxial with a desired reaming trajectory of a shoulder arthroplasty procedure. A space 270 is defined by central body portion 220, adjacent cutting legs 250 and outer frame 280.

Figure 3:
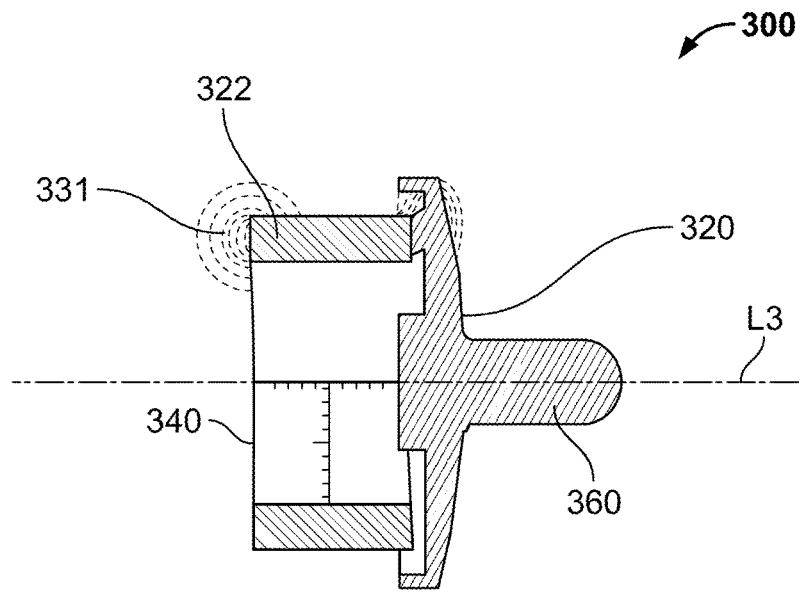
FIG. 3 is a magnetized plot of the magnetized reamer of FIG. 1A

FIG. 3 is shown a magnetic plot of a reamer assembly 300 having a longitudinal axis L3, a bone contacting surface 320 and an opposing distal end surface 340. It can be interpreted that the magnetic field 331 nearest magnet 332 (on the left side of the assembly 300) is around 5000 G, thus an extreme pull force is noted. On the patient side of the assembly 300 (at a post 360 location on the right) this same field is at least an order of magnitude less and quickly falls.

Figure 4:
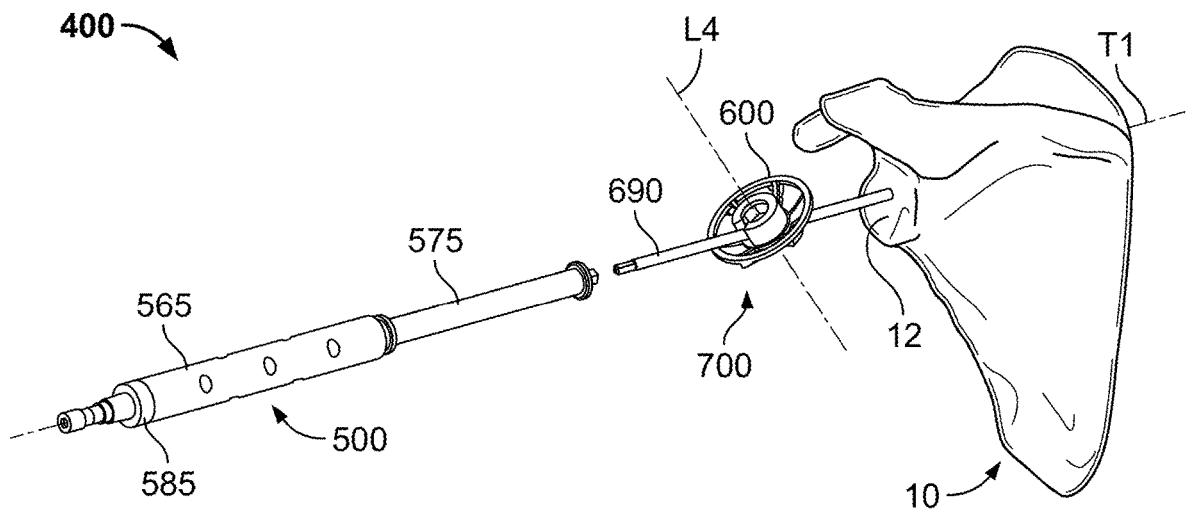
FIG. 4 is an exploded perspective view of one embodiment of a reaming system of the disclosure.

FIG. 4 is an exploded perspective view of a reaming system 400 including a driver assembly 500, a reamer assembly 600 including a guide pin 690. Reamer assembly 600 and guide pin 690 together form a sub-assembly 700. Guide pin 690 is partially within glenoid 12 of scapula 10 along trajectory T1. Reamer assembly 600 has a longitudinal axis L4 that is transverse to T1 when guide pin 690 is within an aperture of reamer assembly 600 and reamer assembly 600 is not engaged to glenoid 12.

Figure 5A:
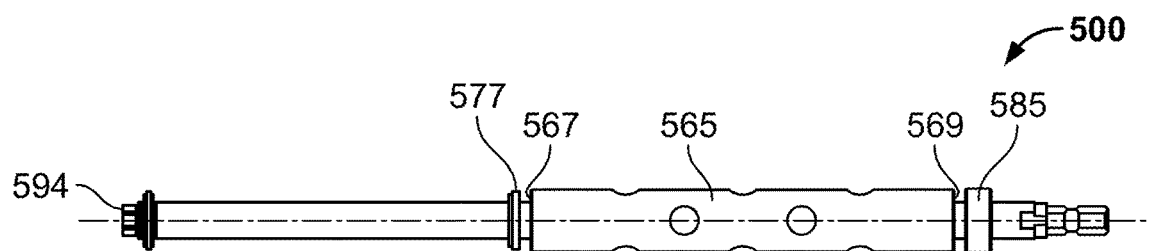
FIG. 5A is a side view of a driver assembly shown as part of the reaming system of FIG. 4.
Figure 5B:
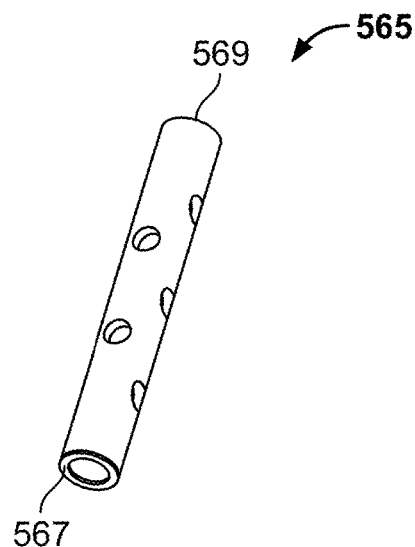
FIG. 5B is a perspective view of one embodiment of a driver sleeve of the driver assembly shown in FIG. 5A
Figure 5C:
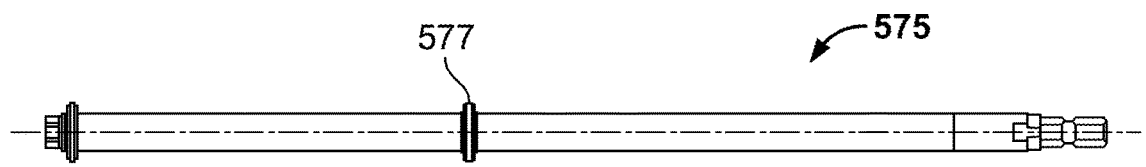
FIG. 5C is a side view of one embodiment of a driver shaft of the driver assembly shown in FIG. 5A.
Figure 5D:
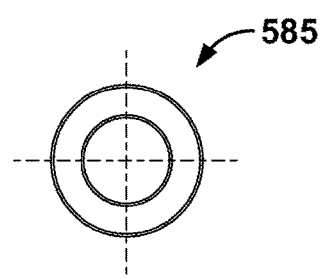
FIG. 5D is a top view of one embodiment of a driver collar of the driver assembly shown in FIG. 5A.

Driver assembly 500 is shown in FIG. 5A, and includes a driver sleeve 565, a driver shaft 575, and a driver collar 585 as shown in FIGS. 5B, 5C and 5D respectively. Driver shaft 575 is cannulated such that a guide pin or k-wire, for example, can be inserted therethrough. Driver shaft 575 is slid through cannulated driver sleeve 565 until a first end 567 of driver sleeve 565 lies adjacent stop portion 577 of driver shaft 575. Driver shaft 575 is then slid through driver collar 585 until driver collar 585 lies adjacent a second end 569 of driver sleeve 565. Driver shaft 575 further includes a driver end portion 592 and a reamer assembly coupling portion 594. Reamer assembly coupling portion 594 is adapted to be coupled to an inner surface of a reamer body of a reamer assembly adjacent the coupling of a reamer housing and the reamer body.

Figure 6A:
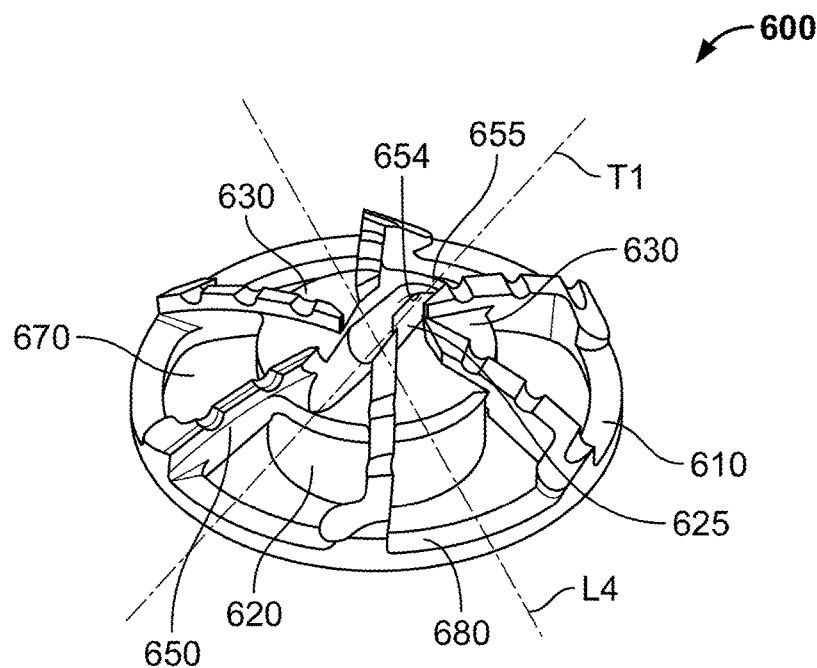
FIG. 6A is a bottom perspective view of a reamer assembly shown as part of the reaming system of FIG. 4.

FIG. 6A is a bottom perspective view of a reamer assembly 600 including a reamer body 610, a magnet 632 and a reamer housing 633. When assembled together, a portion of reamer body 610 and reamer housing 633 form a cannulated central body portion 620 having a bone contacting surface 630 and an opposing distal end surface 640 and an aperture 625 therethrough. Aperture 625 is extended laterally from a central portion of reamer body 610 and is bound adjacent a periphery 655 thereof. Here, central body portion 620 is closed such that a guide pin, for example, cannot be laterally slid into aperture 625, but rather guide pin must be inserted through aperture 625 at an angle transverse to L1 and more in line with T1. Reamer body 610 includes a plurality of cutting legs 650 and an outer frame 680. A space 670 is defined by central body portion 620, adjacent cutting legs 650 and outer frame 680.

Figure 6B:
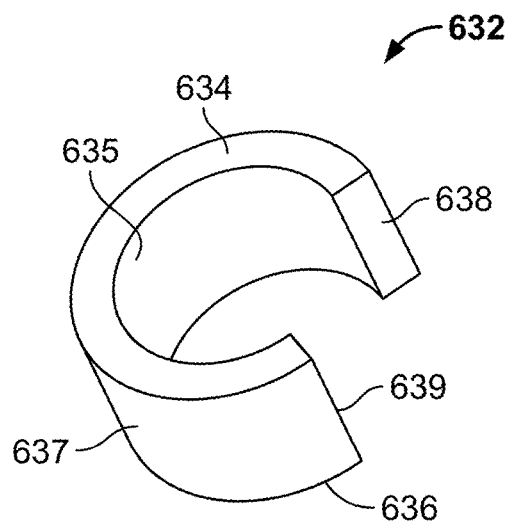
FIG. 6B is a perspective view of one embodiment a reamer magnet of the reamer assembly shown in FIG. 6A.
Figure 6C:
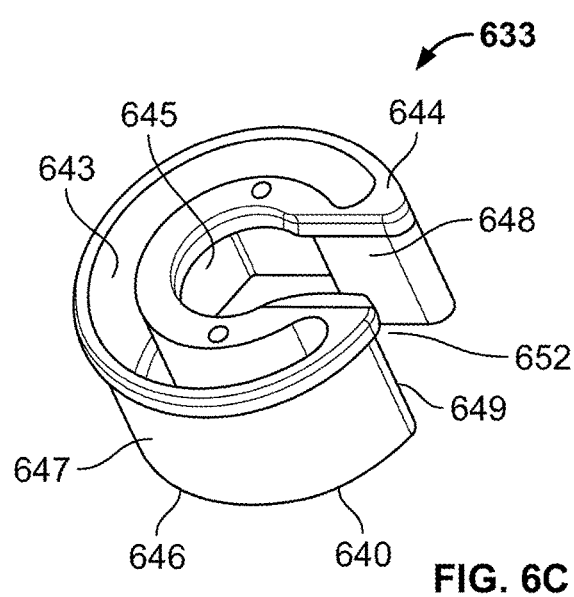
FIG. 6C is a perspective view of one embodiment of a reamer housing of the reamer assembly of FIG. 6A.

As shown in FIG. 6B, magnet 632 includes an upper surface 634, an inner surface 635, a lower surface 636, an outer surface 637 and opposed side surfaces 638, 639 defining a space therebetween. As shown in FIG. 6C, reamer housing 633 includes an upper surface 644, an inner surface 645, a lower surface 646, an outer surface 647 and opposed side surfaces 648, 649 defining a space 652 therebetween. A slot 643 is defined in reamer housing 633 for receipt of magnet 632.

Figure 7:
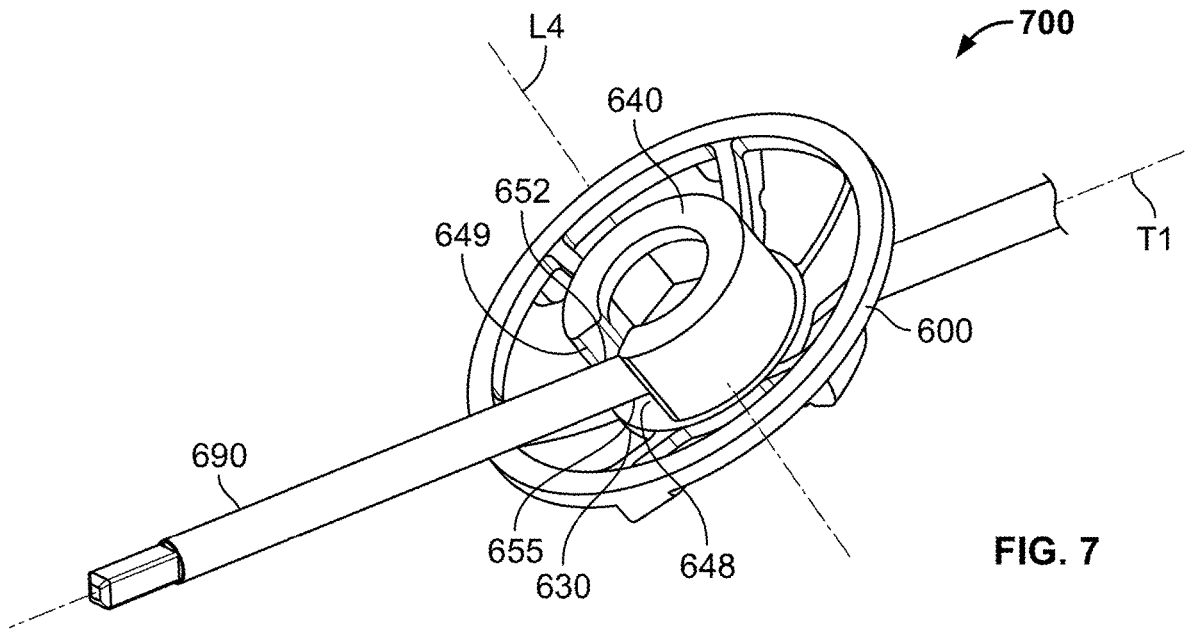
FIG. 7 is a top perspective view of the reamer assembly of FIG. 6A having a guide pin received at an angle to a central longitudinal axis of the reamer assembly.

Inner wall surface 645 and opposing outer wall surface 647 of cannulated central body portion 620 define a thickness and bone contacting surface 630 and opposing distal end surface 640 defining a length. Inner wall surface 645 defines bore or aperture 625 about central longitudinal axis L4 of cannulated central body portion 620. Outer frame 680 defines a periphery of reamer assembly 600, outer frame 680 being coupled to a lateral end of each of the plurality of cutting legs 650. As shown in FIG. 7, cannulated central body portion 620 of reamer assembly 600 forms an opening extending entirely through the thickness and only partially though the length from a location along the length above bone contacting surface 630 and through the opposing distal end surface 640.

Bore 625 and space 652 form a transverse inner opening for receipt of guide pin 690 at an angle to central longitudinal axis L4. Reamer housing 633 coupled to reamer body 610 defines a u-shaped opening bound by base surface 654 and first and second planar surface sections 648, 649. The u-shaped opening is designed to maximize the angulation of reamer assembly 600 over guide pin 690. The u-shaped opening may be defined by base surface 654 intermediate first and second planar surface sections 648, 649, the first and second planar sections 648, 649 separated by a width of recess 652, which has a length defined by a linear distance between opposing distal end surface 640 and base surface 654.

A plurality of reamer apertures 670 are defined by opposing outer wall surface 647 of cannulated body portion 620, adjacent cutting legs 650 and outer frame 680. In one embodiment, recess 652 and one of the plurality of reamer apertures 670 form a transverse outer opening for receipt of guide pin 690 at an angle to central longitudinal axis L4.

In one method of performing minimally invasive surgery using reamer assembly 700 for example. The method comprising sliding guide pin 690 at an angle to central longitudinal axis L4 of reamer assembly 600 through a transverse opening in cannulated central body portion 620 of reamer assembly 600. Cannulated central body portion 620 has a recess 652 through an inner wall surface 645, an opposing outer wall surface 647, and a distal end surface 640. Inner wall surface 645 defines a bore 625 having defining central longitudinal axis L4, bore 625 and recess 652 together form the transverse opening. The method further includes positioning a bone contacting surface 630 of reamer assembly 600 against a desired bone to be reamed such as glenoid 12, for example, and rotating guide pin 690 until a central axis (substantially aligned with T1) of guide pin 690 is substantially co-linear with central longitudinal axis L4 of bore 625 of reamer assembly 600.

In one embodiment of this method, it further comprises sliding cannulated shaft 575 over guide pin 590 until cannulated shaft 575 is coupled to reamer assembly 600, the cannulated shaft 575 closing recess 652.

Figure 8:
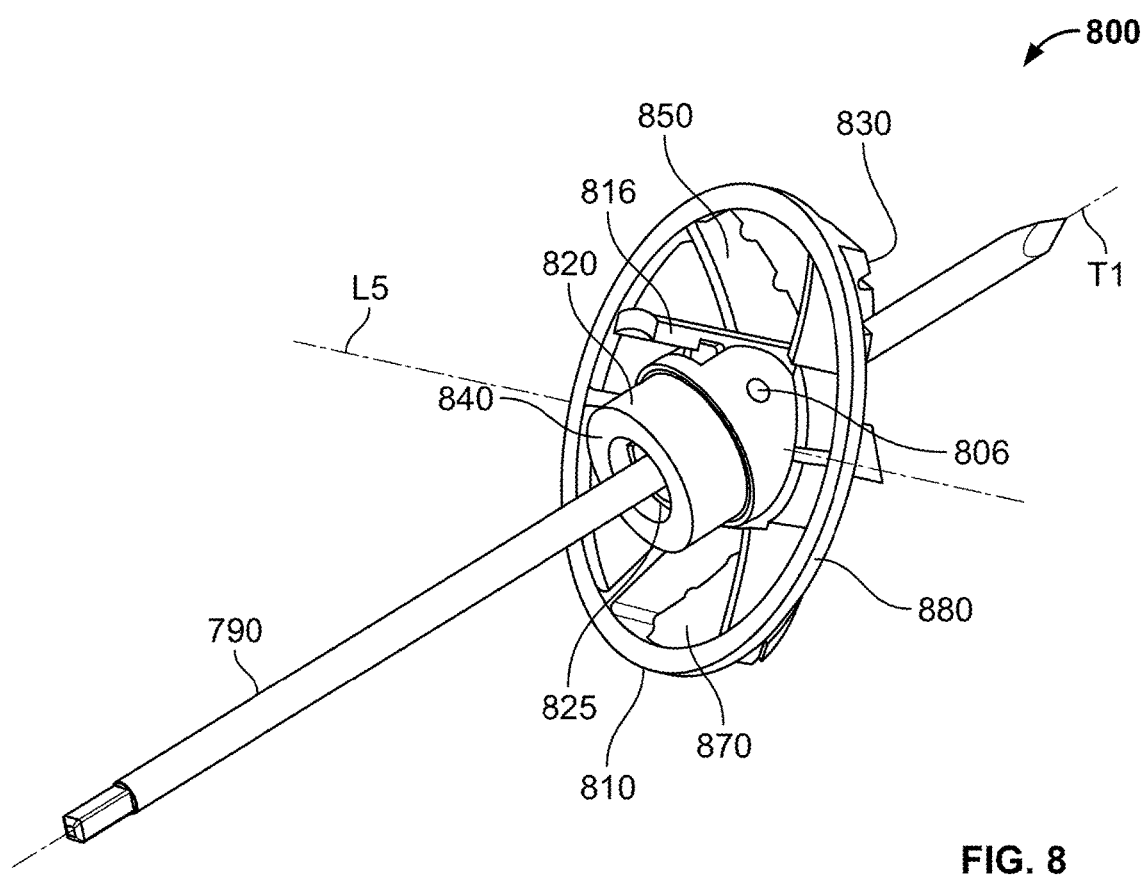
FIG. 8 is perspective view of another embodiment of a reamer assembly of the disclosure having a guide pin received at an angle to a central longitudinal axis of the reamer assembly.

FIG. 8 is perspective view of another embodiment of a reamer assembly 800. A guide pin 690 is received through reamer assembly 800 at an angle to a central longitudinal axis L5 of reamer assembly 800. Reamer assembly 800 includes a hinge 806 between a central body portion 820 and a reamer body 810 where the angle between central longitudinal axis L5 and T1 can be changed via rotation of central body portion 820 about hinge. Reamer assembly 800 further includes a latch 816 that in an open position allows central body portion 820 to rotate with respect to reamer body 810 and in a closed position fixes the location of the central body portion 820 with respect to reamer body 810.

When assembled together, a portion of reamer body 810 and cannulated central body portion 820 have a bone contacting surface 830 and an opposing distal end surface 840 and an aperture 825 therethrough. Reamer body 810 includes a plurality of cutting legs 850 and an outer frame 880. A space 870 is defined by central body portion 820, adjacent cutting legs 850 and outer frame 880.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A reamer system comprising:
   a reamer having a cannulated central body portion having an inner wall surface and an opposing outer wall surface defining a thickness and a bone contacting surface and an opposing distal end surface defining a length, a recess extending entirely through the thickness and only partially though the length, the inner wall surface defining a bore about a central longitudinal axis of the cannulated central body portion; and
   a guide pin having a diameter and a length, the diameter of the guide pin being less than a width of the recess, wherein the bore and the recess form a transverse opening for receipt of the guide pin at an angle to the central longitudinal axis.

2. The reamer of claim 1, wherein the recess is u-shaped and defined by a curved base surface intermediate first and second planar surfaces.

3. The reamer of claim 1, wherein the recess is defined by a base surface intermediate first and second planar surfaces defining the width of the recess.

4. The reamer of claim 3, wherein the recess extends from a location along the length the reamer above the bone contacting surface and through the opposing distal end surface, the recess having a length defined by a linear distance between the opposing distal end surface and the base surface of the recess.

5. The reamer of claim 1, wherein the opposing outer wall surface of the cannulated central body is circular and the plurality of cutting legs extend radially from the opposing outer wall surface.

6. The reamer of claim 1, wherein a plurality of reamer apertures are defined by the opposing outer wall surface of the cannulated body portion, adjacent cutting legs and the outer frame.

7. The reamer of claim 6, wherein the recess and one of the plurality of reamer apertures form a transverse outer opening for receipt of a guide pin at an angle to the central longitudinal axis.

8. The reamer of claim 1, further comprising a plurality of cutting legs extending outwardly from the cannulated central body portion.

9. The reamer of claim 8, further comprising an outer frame defining a periphery of the reamer, the outer frame coupled to a lateral end of each of the plurality of cutting legs.

10. The reamer of claim 8, the plurality of cutting legs are each coupled at a medial end thereof to the bone contacting surface of the cannulated central body portion.

11. The reamer of claim 8, wherein the opposing outer wall surface of the cannulated central body is circular and the plurality of cutting legs extend radially from the opposing outer wall surface.

* * * * *